United States Patent

Heidenreich et al.

(10) Patent No.: US 9,020,828 B2
(45) Date of Patent: Apr. 28, 2015

(54) REFERENCING OF PATIENT-RELATED INFORMATION IN A DISTRIBUTED MEDICAL SYSTEM

(75) Inventors: Georg Heidenreich, Erlangen (DE); Gerhard Weller, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1209 days.

(21) Appl. No.: 12/213,232

(22) Filed: Jun. 17, 2008

(65) Prior Publication Data

US 2009/0006134 A1    Jan. 1, 2009

(30) Foreign Application Priority Data

Jun. 18, 2007    (DE) .......................... 10 2007 027 915

(51) Int. Cl.
*G06Q 50/00* (2012.01)
*G06F 17/30* (2006.01)
*G06Q 10/00* (2012.01)
*G06F 19/00* (2011.01)
*G06Q 50/22* (2012.01)
*G06Q 50/24* (2012.01)

(52) U.S. Cl.
CPC ................ *G06Q 10/00* (2013.01); *G06F 19/32* (2013.01); *G06F 17/30545* (2013.01); *G06Q 50/22* (2013.01); *G06Q 50/24* (2013.01)

(58) Field of Classification Search
USPC ......................................................... 707/770
See application file for complete search history.

(56) References Cited

U.S. PATENT DOCUMENTS

| | | | | |
|---|---|---|---|---|
| 6,263,330 B1 * | 7/2001 | Bessette | ................................ | 1/1 |
| 6,826,564 B2 * | 11/2004 | Thompson et al. | ........... | 707/770 |
| 6,944,610 B2 * | 9/2005 | Moore et al. | ........................... | 1/1 |
| 7,386,462 B2 | 6/2008 | Silva-Craig et al. | | |
| 7,921,131 B2 * | 4/2011 | Uppala | ......................... | 707/770 |
| 8,090,686 B2 * | 1/2012 | Rowley | ........................ | 707/613 |
| 2002/0194162 A1 * | 12/2002 | Rios et al. | ......................... | 707/3 |
| 2003/0037097 A1 * | 2/2003 | Meyer et al. | .................. | 709/202 |
| 2008/0033958 A1 * | 2/2008 | Richards et al. | .................. | 707/9 |

FOREIGN PATENT DOCUMENTS

| | | | | |
|---|---|---|---|---|
| DE | 19901438 A1 | 5/2000 | | |
| DE | 10211579 A1 | 10/2002 | | |
| WO | WO 9724685 | * | 7/1997 | ........ G06F 17/30545 |

* cited by examiner

*Primary Examiner* — Anita Coupe
(74) *Attorney, Agent, or Firm* — Harness, Dickey & Pierce, P.L.C.

(57) ABSTRACT

A method, a system and a computer program product are disclosed for referencing medical electronically available patient-related data records which are stored in a distributed manner in a computer-based network, including a multiplicity of computer-based entities. In at least one embodiment, a request for patient-related data records is generated on the basis of an original identifier and is sent to an index server. By accessing a table, the index server checks whether entries or data records are stored for the respective patient in the respective repository. If so, it inserts this reference to the storage location into the result. The request is forwarded from index server to index server until all index servers have been processed, so that the end result can be forwarded to the requesting workstation with all references to requested patient-related data records.

19 Claims, 1 Drawing Sheet

REFERENCING OF PATIENT-RELATED INFORMATION IN A DISTRIBUTED MEDICAL SYSTEM

PRIORITY STATEMENT

The present application hereby claims priority under 35 U.S.C. §119 on German patent application number DE 10 2007 027 915.0 filed Jun. 18, 2007, the entire contents of which is hereby incorporated herein by reference.

FIELD

Embodiments of the invention generally relate to the fields of medical engineering and data processing, particularly data organization in a distributed system.

At least one embodiment of the invention relates particularly to a method, a system and/or a computer program product for referencing medical, electronically available patient-related data records which are stored in a distributed manner in a computer-based network which includes a multiplicity of medical engineering entities.

BACKGROUND

In the past, information, particularly patient-related information, was usually provided only within an organizational unit (hospital, clinic, doctor's practice etc.). Thus, users who had computer network access within this facility could usually also access the patient-related data.

It is found to be a problem within this context that the patient-related data are usually stored in a distributed manner (e.g. in the respective departments of a hospital) and usually do not have any indexing. A quick and simple message concerning the question as to whether or not data records exist for a particular patient and, if so, where, without actually accessing the data is either not possible at all in the prior art or is possible only with the aid of time-consuming IT searches. Provision of patient-related data records beyond the boundaries of the institution (that is to say also outside of the respective clinic, outside of the doctors' practice, possibly even beyond national borders) has likewise not been possible to date.

However, as part of the health reform, it is meant to be possible for different institutions (e.g. hospitals, clinics, doctors' practices, health insurance companies etc.) to provide their data or the databases connected to them over the Internet. The entire health-related network therefore comprises different institutions with their databases and individual connected entities, in some cases beyond national borders. Health-related, computer-based, patient-related information is now meant to be available over a public network (e.g. the Internet). In this context, the problem arises, inter alia, that it is relatively difficult or complex to identify or find an individual patient-related data record within the distributed network without actually having to access the data record.

SUMMARY

In at least one embodiment, the present invention demonstrates a way of permitting cross-network analysis of whether or not patient-related entries exist and, if so, where they exist without necessarily having to provide the content of the data. The data are merely intended to be referenced. In other words, it would be possible for the user to obtain an indication of where the requested patient-related data records are stored and can be found within the system.

Embodiments of the method is described below. Features or alternative embodiments and/or advantages mentioned within this context can likewise be transferred to the system and/or to the computer program product, and vice versa. In other words, the system and/or the computer program product can also be developed using the features which relate to the method. The corresponding functional features of the method are formed by appropriate hardware modules of the system.

The invention, in at least one embodiment, relates particularly to a method for referencing and/or indexing medical, electronically available, patient-related data records which are stored in a distributed manner in a computer-based network, comprising a multiplicity of entities, the method being carried out on a computer, having the following method steps:

detecting a request for references to patient-related data records, on the basis of an original identifier;

converting or translating the original identifier into at least one search criterion if the entities to be interrogated require another identifier as identification mechanism;

searching for and detecting at least one reference for the requested patient-related data records, on the basis of the original identifier and/or the at least one search criterion, and outputting a result, comprising at least one reference to the requested patient-related data records.

Within the context of at least one embodiment of this invention, the term "referencing" is to be understood as an indication of a storage location for patient-related data records. In other words, a reference to data is provided and not the data per se. The referencing is therefore of a pointer, index or indication nature and allows a simple response to the question regarding whether or not entries exist for the requested patient-related data records and, if so, where these are stored.

The patient-related data records may be all health-related information pertaining to a patient. This may include not only purely medical data (X-ray images, findings reports etc.) but also administrative data (health insurance status, type of insurance, time of referral to a clinic etc.). The patient-related data records may be in any formats (e.g. DICOM etc.) in image and/or text data.

In this case, the network can be understood to be very comprehensive and particularly to span clinics. The network, therefore comprises a multiplicity of entities, such as clinical facilities, hospitals, doctors' practices, health insurance companies, possibly the latter's connected databases for clinical studies with the patients, for example.

The entities are computer-based and have network access (usually by means of Internet access).

The invention, in at least one embodiment, provides an identification mechanism which allows patient-related data records to be identified within the network. In principle, a plurality of identification mechanisms are possible in this case, depending on the type of entity interrogated. By way of example, the hospital A may require a different identification mechanism (e.g. using a combination of the hospital-identification, patient-name and date-of-birth statements) than the clinical facility B (which uses the health insurance identification number, for example). In line with the invention, the respective identification mechanism is used dynamically. Firstly, an original identifier is provided which the user uses to denote or identify the respective patient. This can be done using the patient name, a health insurance identification, a combination of patient-related information, such as the clinic and a patient name, or using other patient identifications. Usually, the original identifier is chosen such that it is as user friendly as possible.

Normally, the patient name will be part of the original identifier, so as to avoid errors as far as possible, in order to avoid input of numeral-based identifiers. The method may be used, in at least one embodiment, in this context for converting the identification mechanisms is similar to or based on the DNS servers known from the Internet, or for the purposes of dynamic updating the DDNS or dynD DNS servers. Alternatively, however, hybrid forms or other original identifiers, for example using a health insurance identification number, are also conceivable here.

Depending on which entities are interrogated, provision is made for the original identifier to be translated into one or more search criteria which is/are used to send a request to the respective entity regarding whether or not the requested patient-related data records are stored in the entity. In line with at least one embodiment of the invention, identification mechanisms can be converted or translated a plurality of times. This is done particularly if a plurality of entities need to be interrogated for patient-related data records. In one preferred embodiment, the conversion is made using a lookup table which allows association between the respective identification mechanisms of the different entities. The identification mechanism (comprising the original identifier and the at least one search criterion) is based on indexing of the data records.

The associative relation between the different identification mechanisms (e.g. between the original identifier and a search criterion or between a first search criterion and further search criteria) is usually surjective. That is to say that a first entry in a first identification mechanism may also comprise a plurality of entries in a second identification mechanism. This splits the search for patient-related data records into a plurality of search trees.

In an example embodiment, the result of the inventive method includes at least one indication of or reference to the requested patient-related data records. The result therefore also contains a statement regarding whether or not entries exist on the basis of requested data records and, if so, where they are stored. The result is therefore the response to the request and comprises not only the patient identification but also at least one reference to the respective data records found, for example in the form of a URL (Uniform Resource Locator) statement for identifying a resource and the storage location of the resource in the computer network, such as the Internet. Alternatively, a general identification indication may also be provided in the form of a URI (Uniform Resource Identifier). The result therefore comprises a type of pointer to the requested patient-related data records. Usually, the result will comprise a list of references, since there are usually a plurality of entries for a patient (for example in the form of several hospital stays and, by way of example, examinations performed by registered doctors).

In one example embodiment of the invention, all or selected steps of the method are carried out automatically. Preferably, the detection, the conversion, the search and the detection and/or the output of the result are performed automatically.

At least one embodiment of the inventive method is based on a request for patient-related data records and on a response based on this. In the example embodiment, the request comprises at least the patient identification,
a statement regarding who requires the information (e.g. Internet address, name, network node, application entity etc.),
an identification mechanism, particularly an original identifier, which is used to identify the patient for the request,
further identification mechanisms, e.g. in the form of at least one search criterion, in order to identify the patient-related data records in a particular entity. The search criteria or the further identification mechanisms are variable and flexible, and therefore a plurality of identification mechanisms may be used within a search;
a list of processed or visited entities or network nodes. This statement allows the user to be provided with information about which entities have been questioned for his request up to the present time or overall. In addition, this can safely prevent endless loops.

In the example embodiment, the response to the request or the result includes the same fields as the request itself (see listing above) and, furthermore, comprises a URI/URL list containing references to patient-related information. In addition, it is possible for the request and/or the result also to comprise further fields.

Alternatively, it is also possible for the actual request to contain a "to be visited" list. In other words, it is possible for the actual creation of a request to involve stipulating which network nodes or entities are to be interrogated. This allows the search for references to be restricted and hence speeded up.

In the example embodiment, the result merely includes a reference to the requested patient-related data records. In a more complex embodiment of the invention, however, provision may also be made for a further method step likewise to load the results found. In particular, this is done after certain loading criteria have been met. The loading criteria are usually security checks, authentication measures by the entity and/or by the user. This ensures that only an authorized user can access the data.

As already mentioned, the different entities are usually based on different identification mechanisms. In other words, different identifiers and/or search criteria are required in order to be able to reference the data records. At least one embodiment of the invention therefore provides automatic conversion of identification mechanisms. Depending on which entity is being interrogated, the respective correct identification mechanism is used. In particular, the original identifier is converted into at least one search criterion. The further identification mechanisms can be detected together in one method step or—alternatively—it is also possible for the conversion always to be performed on a situational basis in the context of the respective entity and hence a plurality of times.

In the example embodiment, the method is based on a multiplicity of what are known as index servers, which are intended to process incoming requests according to patient-related data records. The input variable (Input) used for an index server is the request with an original identifier for identifying the respective patient. The output variable (Output) used for the index server is an appropriate entry into the result (that is to say a reference which has been found) and forwarding to a further index server (for the purpose of the continued search for further references). A request for references is thus forwarded to a first index server, which then forwards the request to further index servers until all index servers have been processed. The index servers which detect a reference to the requested patient-related data records enter this reference into the result. When the last index server has been processed or following an entry into the result list with references which have been found, the requesting workstation is provided with the result (containing a list of references). If no information pursuant to the respective patient is stored in the network, this list is empty.

In one example embodiment, the list of the index servers to be visited can also be restricted in advance in order to make the search more specific.

If the request has already been forwarded (from a first index server to further index servers), the visited list thus includes those index servers which have already been visited to date for the purpose of responding to the request. Furthermore, the "to be visited" list may also be carried (containing index servers which are still to be questioned).

In one example embodiment, an index server processes an incoming request by:

1. Renaming: replication of the request for forwarding to a plurality of index servers, possibly with the original identifier being converted into further identification mechanisms (e.g. search criteria);
2. Resolution: a reference is detected and recorded as a result if the respective identification mechanism is on an indicator list in the respective index server. Thus, in other words, if the index server provides information that it contains references which match the respective identifier or identification mechanism, this reference is stored.
3. Delegation: the request is forwarded to further index servers. To avoid endless loops in this case, preferably at least one list is managed, namely the visited list. From the set of all possible index servers, the ones which have already been visited are identified. These are not visited again.

In one example embodiment of the invention, the request and/or the result are transmitted using a standardized, asynchronous Internet protocol, for example using SMTP, HTTP, HTTPS etc. In addition, further protocols may be used in order to ensure the transport of further messages.

In another example embodiment, the identification mechanism is based on identification of the outputting entity (organization or hospital department). The identification mechanism is therefore based both on patient identification and on entity identification. In other words, the identification mechanism is component-based and comprises identification of the domain (entity) and identification of the person (patient), as stipulated in the ISO/IEC9834/1 standard using the identification mechanism "OID", for example. In alternative embodiments, the identification mechanism may comprise other components, which are concatenated or appended by a further separating symbol (dot), for example.

In another embodiment of the invention, it is possible to restrict the result list if only certain documents need to be referenced. This is possible, by way of example, when the doctor is searching only for patient-related information in a certain time interval. It is then possible to add a further "finding/procedure date" field.

Alternatively, the result may also be restricted by further restrictive measures, for example by intending that only those references which correspond to a particular medical code be output. In this case, such a further field is added. Furthermore, other additional fields are also conceivable, depending on the instance of application.

Another feature of at least one embodiment of the invention is characterized by the result being sorted according to different sorting criteria (for example date, frequency of hits etc.).

In the example embodiment, the computer-based network comprises the following entities: the index servers, the registries and the repositories.

The repositories and registries may be in the form of two separate modules of a database. In this context, the repositories may either contain the data themselves or contain just an indication (reference in the form of a link) of the data, while the registries contain particularly metadata for the data stored in the repositories. The registry thus stores data which allow a response to the question "Is there an entry with the respective patient identification in the repository: Yes or No?". The registries thus include just an indication of the data stored or referenced in the repository. One advantage which arises from the split between repository and registry can be seen as being that referencing in the registries and/or updates in the index servers can be performed at time intervals which are independent of the time of the communication with the current repositories. Overall, the method can therefore be made more efficient.

Another advantage of at least one embodiment of the inventive method can be seen in the use of asynchronous protocols. This makes it possible to ensure that the first results are provided immediately after they are detected. In other words, at least one embodiment of the invention allows a first reference to the requested patient-related data records to be output immediately while the other references are ascertained in the background. In other words, it is not necessary to wait for the end of the request in order for the result to be able to be output, but rather the result can be output in successive interim steps.

It is also found to be advantageous in practice that the existing infrastructure can be used with existing networks and their nodes.

At least one embodiment is achieved by a computer program product having the aforementioned features.

At least one embodiment is achieved by a system for referencing medical, electronically available, patient-related data records, having:
- a computer-based network, comprising a multiplicity of entities which store or reference patient-related data records in a distributed manner,
- a request generator which is intended to generate and/or detect a request for references to patient-related data records, with an original identifier being used as input variable,
- a conversion unit which is intended to convert the original identifier into at least one search criterion if the entities require another identifier as identification mechanism,
- an index server which is intended to search for at least one reference for the requested patient-related data records and to detect the storage location thereof as a reference, on the basis of the original identifier and/or the at least one search criterion, and which is also intended to forward the request to further index servers, and
- an output unit which is intended to output a result or a partial result which comprises at least one reference to the requested patient-related data records.

In one example embodiment, the system also comprises a registry and/or a repository which are associated with a respective index server. Either the repository stores the patient-related data records directly or they contain a reference to the storage location for the patient-related data records. The data records are available in indexed form. In this case, the identification mechanism identity mechanism is automatically and dynamically adapted to the respective index. Usually, the data records are indexed in a preprocessing phase of the method, this indexing being carried out by an indexing module. The registry comprises metainformation about the data which are stored in the respective repository. In other words, the registry contains a list containing identification mechanisms (that is to say containing patient identifiers, for example), together with an entry "Present/Absent". In other words, the registry merely contains information about which patient-related data are stored in the respective repository and which are not. This allows a rapid response or a rapid entry in the result.

BRIEF DESCRIPTION OF THE DRAWINGS

The detailed description of the figures below discusses example embodiments (which are to be understood as non-restrictive) with their features and further advantages with reference to the drawings, in which.

DETAILED DESCRIPTION OF THE EXAMPLE EMBODIMENTS

Figure 1:
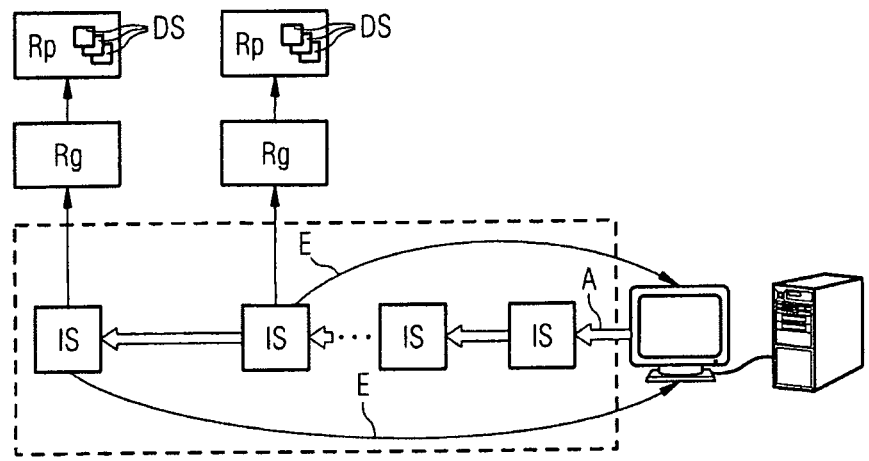
FIG. 1 shows an overview-type illustration of the referencing using a plurality of index servers in line with one example embodiment.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As shown schematically in FIG. 1, a request A for patient-related data records DS is output by a medical workstation. The data records DS may be stored in a repository Rp. The request A for references to patient-related data records DS is based on an original identifier oID. The request A is forwarded to an index server IS, which receives it and processes it.

The request is then forwarded to further index servers IS for further processing. An index server IS takes the original identifier oID and/or a search criterion SK as a basis for making a request to a registry Rg regarding whether or not the requested patient-related data records DS are stored in a repository Rp. Preferably, a respective repository Rp is associated with a registry Rg which, for its part, is in turn associated with an index server IS. Either the repository Rp can store the patient-related data records directly or they contain a further reference to the storage location for the data records DS.

The inventive hierarchical data organization of an embodiment allows a simple lookup table command to establish whether the requested patient-related data records DS are stored in the repository Rp which is associated with the respective index server IS. If the data are stored there, an entry is put into a result E, which can be sent back to the requesting workstation either immediately as a partial result or at a later time all together. If the result following processing by the respective index server IS is that the requested patient-related data records DS are not stored on the associated repository Rp, the request is forwarded to a further index server IS.

Figure 2:
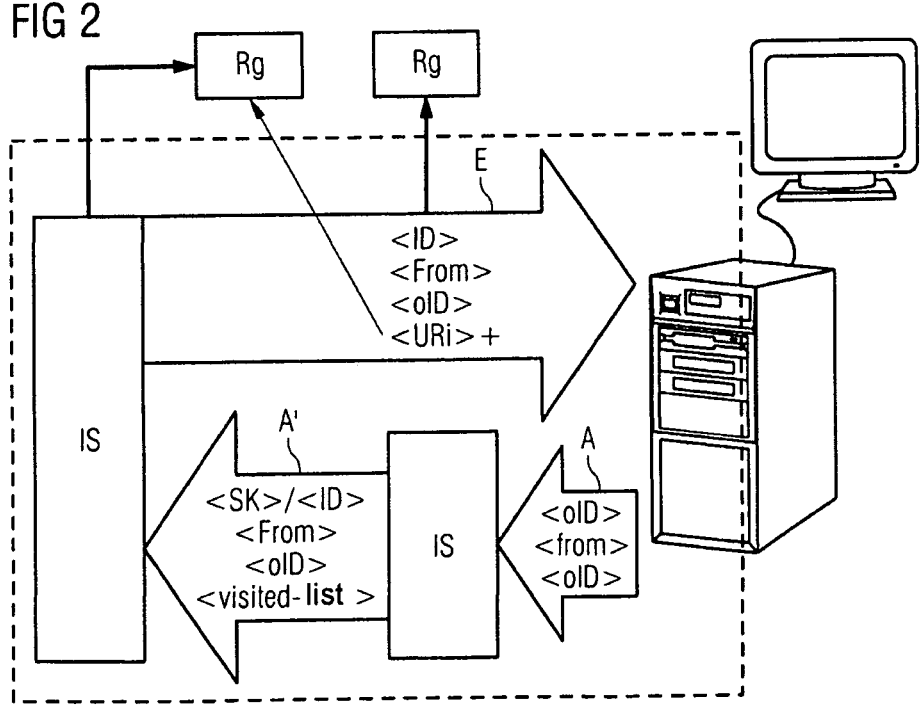
FIG. 2 shows an overview-type illustration of the flow of information in the inventive method in line with one example embodiment.

This is intended to be shown by the arrows in FIG. 1, which point from the respective index server leftwards to the further index server IS and are in the dashed box (likewise in FIG. 2). The requests from the workstation are shown both in FIG. 1 and in FIG. 2 on the right-hand side. The workstation produces a request for patient-related data records DS and obtains the result E in the form of a reference to the requested patient-related data records DS.

In principle, two alternative embodiments are provided in which the result E is routed to the requesting workstation. On the one hand, it is possible for all partial results to be sent to the requesting workstation immediately. In other words, a reference which has been found is output immediately as a partial result as soon as it has been found. Alternatively, it is possible for all references first to be gathered to form a total result E, which is sent to the requesting workstation in a concluding step as a total packet. Preferably, the first alternative is used, since this allows a more efficient workflow.

FIG. 2 again schematically shows which messages have interchanged between the instances involved during the inventive method. The requesting workstation sends the request A to an index server IS. The request A preferably comprises the original identifier oID, a statement regarding who is the originator of the request (that is to say this workstation, for example), and furthermore possibly includes further identification mechanisms.

If the request A is forwarded to further index servers IS, the request A' which is then forwarded comprises not only the previous statements (original identifier oID, statement regarding who created the request A) but also a search criterion, which is used as a further identification mechanism, and a list of entities or network nodes which have already been visited. These are usually index servers IS to which the request has already been forwarded.

When the request A has been processed by all index servers, the last index server IS involved sends a result message E to the requesting workstation. The result message E comprises a patient identification, a statement regarding who sent the request A, the original identifier and, as the result, a reference to the storage location for the requested patient-related data records DS in the form of a URI. The URI points to the storage location within the registry Rg.

In one example embodiment, provision is made for the result E to comprise the same statements or fields as the request A, but additionally to include a reference, for example in the form of a URI list, which comprises the references to the requested patient-related data records DS, instead of the visited list, which the request A, A' contains.

To process the requests A, A', each index server IS persistently stores the following data:
- an indicator list: as a paired association between a patient identification (or a patient identifier) and a reference (URI address) for a registry server Rg, which references data records DS for the respective patient;
- an escape list: a list of references (URI addresses) which refers to other index servers IS which are likewise able to respond to the received request A;
- a master patient index: this index is optional and comprises a list of quadruples (domain-1, identifier-1, domain-2, identifier-2) which allows a suitable patient identification (e.g. ID-1) in the domain-1 to be replaced by another identification mechanism (e.g. ID-2) which can be used in the other domain. In this context, it should be remembered that the master patient index is dynamic and not complete for a patient identification domain. In this case, domain is understood to mean the set of selected entities in the computer-based network. It may coincide with national borders, for example.

In one example embodiment of the invention, an index server IS processes an incoming request A using the following steps:
1. Renaming: If the patient identification (original identifier oID or search criterion SK) matches an identifier in one or more quadruples of the master patient index, a corresponding copy of the request is produced. In this context, the original identification mechanism is possibly (that is to say if necessary) replaced by a new identification mechanism (which is then valid in the next domain).
2. Resolution: If the patient identification is in the indicator list of the index server IS, the index server IS generates a response or a result E which comprises, from a given patient identification <ID>, the relevant reference to the identification in the indicator list, the requesting address <From> and the original identifier <oID> which has been output by the requesting entity.
3. Delegation: For every index server IS which is on the escape list and which is not on the visited list (<visited-list>), the respective index server IS forwards the request A, A' to the next index server IS. In this case, the sending or forwarding index server IS enters its own address into the visited list. This feature allows endless loops to be avoided.

At least one embodiment of the invention is thus based on the output of a request message A which is forwarded to a multiplicity of index servers IS so that they can process it. When all index servers IS have put their entries into the result E, the result E is complete and can be forwarded to the requesting workstation as a response message. Equally, partial results can actually be forwarded to the requesting station in advance.

One fundamental feature can be seen as being that the correct identification mechanism is automatically used for the search in the respective index server IS. If a patient is identified by way of his patient name in a first domain (e.g. hospital A), for example, it may be possible that the same patient in a further domain (e.g. the doctor's practice B) is now not identified exclusively by means of his name, but rather is identified by way of another identification mechanism (e.g. in the form of patient name in combination with date of birth and health insurance number). In line with the invention, the first identification mechanism is automatically transferred or converted to the second. If a wrong or incorrect identification mechanism were to be used for searching in the index server IS in the further domain, no reference would be obtained.

At least one embodiment of the invention provides translation tables or lookup tables for this purpose which convert a first identification mechanism into a further identification mechanism. By way of example, Mr A. N. Other in the domain HOSPITAL A would have the identification xxx, while Mr A. N. Other in the domain HOSPITAL B would have the identification yyy. The conversion and adaptation of the identification mechanisms is provided by the invention automatically and dynamically (on the basis of the domain-specific indexing of the data records).

Finally, it should be pointed out that the description of the invention and the example embodiments are to be understood, in principle, as non-restrictive in respect of a particular physical implementation of the invention. In particular, it is obvious to a person skilled in the relevant art that the invention can be implemented partially or completely in software and/or hardware and/or in a manner distributed over a plurality of physical products—in this case particularly also computer program products.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for referencing medical electronically available patient-related data records which are stored in a distributed manner in a computer-based network including a multiplicity of entities, each associated with an index server, the method comprising:
   detecting, by a first index server, a request by a workstation for references to patient-related data records, the request including an original identifier and a visited list providing information about which entities have been interrogated or are to be interrogated;
   converting, by the first index server, the original identifier into at least one search criterion when the associated entity requires another identifier as an identification mechanism;
   searching at least one registry, by the first index server, for and detecting at least one reference for the requested patient-related data records, based upon at least one of the original identifiers and the at least one search criterion, the at least one reference referencing the requested patient-related data records stored in a repository;
   entering, by the first index server, the at least one reference into at least one of a result and a partial result upon detecting the at least one reference;
   outputting, by the first index server, the at least one of the result and the partial result and forwarding the request to a second index server that has not been interrogated according to the visited list;
   repeating the detecting, converting, searching, and entering steps at the second index server; and
   sending, by a last index server, a result message to the requesting workstation when the request has been processed by all index servers, the result message including the at least one of the result and partial result.

2. The method as claimed in claim 1, wherein the outputting outputs the result and the result allows the referenced requested patient-related data records to be loaded.

3. The method as claimed in claim 1, further comprising:
   converting the at least one search criterion into at least one further search criterion.

4. The method as claimed in claim 1, wherein the converting converts the original identifier into the at least one search criterion and all patient-related data records are provided with an index which allows at least one of identification and access to the data record using the respective identification mechanism, using at least one of the identifier and the search criterion, the indexing of all data records being able to be performed at an independent time.

5. The method as claimed in claim 1, wherein the search for references is performed on a plurality of different entities.

6. The method as claimed in claim 1, wherein the search involves forwarding the request to further entities.

7. The method as claimed in claim 1, wherein the outputting outputs the result and the transmission of at least one of the request and the result is based on a standardized Internet protocol.

8. The method as claimed in claim 1, wherein the search for and detection of a reference for the requested patient-related data records are executed on an index server which stores references to patient-related data records.

9. The method as claimed in claim 1, wherein the converting converts the original identifier into the at least one search criterion and the original identifier and the at least one search criterion uniquely identify at least one of the patient and patient-related data records across entities.

10. The method as claimed in claim 2, wherein the result allows the referenced requested patient-related data records to be loaded after further loading criteria have been met.

11. The method as claimed in claim 1, wherein the converting converts the original identifier into the at least one search criterion and all patient-related data records are provided with an index which allows at least one of identification and access to the data record using the respective identification mechanism using at least one of the identifier and the search criterion, the indexing of all data records being able to be performed at an independent time.

12. The method as claimed in claim 1, wherein the method is based on indexing, wherein all patient-related data records are provided with an index which allows at least one of identification and access to the data record using the respective identification mechanism, the indexing of all data records being able to be performed at an independent time and in advance of the method.

13. The method as claimed in claim 1, wherein the search involves forwarding the request to further index servers.

14. The method as claimed in claim 1, wherein the search involves forwarding the request to further entities with conversion of the original identifier into at least one search criterion.

15. The method of claim 1, further comprising:
broadcasting the request for references to patient-related data records using the at least one search criterion, wherein the converting converts the original identifier into the at least one search criterion.

16. The method of claim 1, wherein the at least one visited list statement includes information about which entities have been interrogated and which need to be interrogated when at least one of searching for and detecting references.

17. The method of claim 1, wherein each index server is associated with one of the at least one registry and the one of the at least one registry is associated with the repository.

18. As system for referencing medical electronically available patient-related data records, comprising:
  a computer-based network, including a multiplicity of entities, each associated with an index server, to store patient-related records in a distributed manner;
  a request generator to detect a request by a workstation for references to patient-related data records, with an original identifier being used as input variable, the request containing a visited list providing information about which entities have been interrogated or are to be interrogated;
  a conversion unit of a first server to convert the original identifier into at least one search criterion when the associated entity requires another identifier as identification mechanism;
  the first index server to search at least one registry for a least one reference for the requested patient-related data records and to detect the storage location thereof as a reference, based upon at least one of the original identifier and the at least one search criterion, the at least one reference referencing the requested patient-related data records stored in a repository, the index server configured to enter the reference into at least one of a result and a partial result;
  an output unit of the first server to output the at least one of the result and the partial result and forward the request to a second index server that has not been interrogated according to the visited list;
  a conversion unit of a second server to convert the original identifier into at least one additional search criterion when the associated entity requires another identifier as identification mechanism;
  the second index server to search at least one additional registry for a least one additional reference for the requested patient-related data records, based upon at least one of the original identifier and the at least one additional search criterion, the at least one additional reference referencing the requested patient-related data records stored in a repository; and
  a send unit in a last index server that has not been interrogated, the send unit configured to send a result message to the requesting workstation when the request has been processed by all index servers, the result message including the at least one of the result and the partial result.

19. A non-transitory computer readable medium including program segments for, when executed on a computer device on a network including a multiplicity of entities, each associated with an index server, causing the network to:
  detect a request by a workstation for references to patient-related data records, based, the request including an original identifier and a visited list providing information about which entities have been interrogated or art to be interrogated;
  convert, by the first index server, the original identifier into at least one search criterion when the associated entity requires another identifier as an identification mechanism;
  search at least one registry, by the first index server, for and detecting at least one reference for the requested patient-related data records, based upon at least one of the original identifier and the at least one search criterion, the at least one references referencing the requested patient-related data records stored in a repository;
  enter, by the first index server, the at least one reference into at least one of a result and a partial result upon detecting the at least one reference;
  output, by the first server, at least one of a result and a partial result to and forward the request to a second index server that has not been interrogated according to the visited list;
  repeat the detecting, converting, searching, and entering steps at the second server; and
  send, by a last index server that has not been interrogated, a result message to the requesting workstation when the request has been processed by all index servers, the result message including the at least one of the result and the partial result.

* * * * *